(12) United States Patent
Vetter et al.

(10) Patent No.: US 6,398,762 B1
(45) Date of Patent: Jun. 4, 2002

(54) SYRINGE NEEDLE PROTECTOR

(75) Inventors: Helmut Vetter, Ravensburg; Thomas Otto; Joachim Glocker, both of Weingarten, all of (DE)

(73) Assignee: Arzneimittel GmbH Apotheker Vetter & Co. Ravensburg, Ravensburg (DE)

( * ) Notice: Subject to any disclaimer, the term of this patent is extended or adjusted under 35 U.S.C. 154(b) by 0 days.

(21) Appl. No.: 09/454,187

(22) Filed: Dec. 3, 1999

(30) Foreign Application Priority Data

Dec. 5, 1998 (DE) ........................... 198 56 167

(51) Int. Cl.[7] ................................. A61M 5/32
(52) U.S. Cl. .................. 604/199; 604/171; 604/192
(58) Field of Search ........................ 604/192, 197, 604/198–199, 187, 171, 231, 200–201, 241, 232

(56) References Cited

U.S. PATENT DOCUMENTS

| 4,795,432 A | * | 1/1989 | Karczmer |
| 5,549,568 A | * | 8/1996 | Shields |
| 5,658,259 A | * | 8/1997 | Pearson et al. |
| 5,688,251 A | * | 11/1997 | Chanoch |
| 5,894,015 A | * | 4/1999 | Rechtin |
| 5,971,966 A | * | 10/1999 | Lav |

* cited by examiner

*Primary Examiner*—Sharon Kennedy
*Assistant Examiner*—Catherine Serke
(74) *Attorney, Agent, or Firm*—Herbert Dubno; Andrew Wilford

(57) ABSTRACT

A syringe has a syringe body having an outer end, a needle holder on the outer end, a needle fixed on the needle holder so that liquid in the body can be expressed through the needle, and a cap removably fitted to the body over the needle holder and enclosing the needle holder and needle. A flexible envelope engaged over the needle has an inner end fixed to the needle holder and an outer end adapted to be easily pierced by the needle. The envelope is compressible parallel to the needle. The envelope is generally cylindrical and formed as a cuff, for instance with annular corrugations allowing it compress axially very easily.

12 Claims, 4 Drawing Sheets

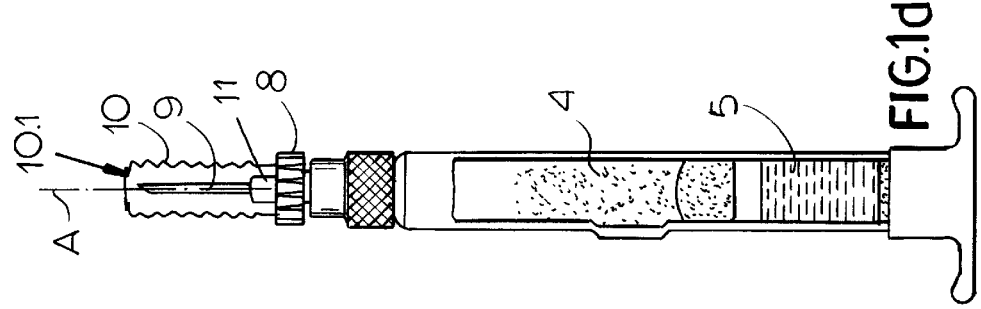
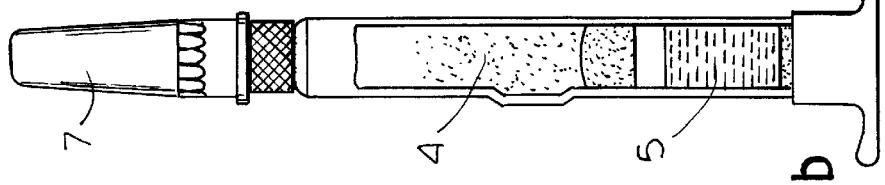
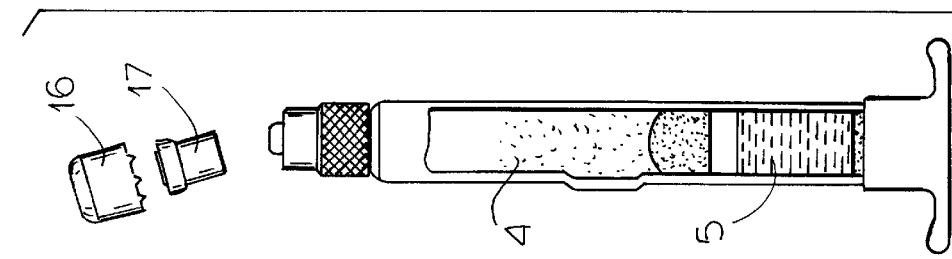
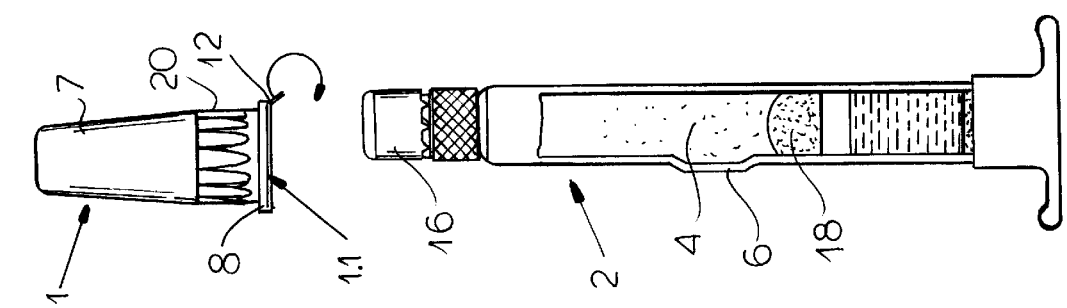

SYRINGE NEEDLE PROTECTOR

FIELD OF THE INVENTION

The present invention relates to a syringe. More particularly this invention concerns a needle protector for a syringe, carpule, or the like.

BACKGROUND OF THE INVENTION

A syringe of the standard, carpule, or PEN type typically has a tubular body with a rear end fitted with a plunger and a front end adapted to carry a needle holder on which is mounted a cannula or needle. The plunger is advanced to express liquid in the body out through the needle. It is standard to provide a protective cap over the needle both to maintain it sterile and to protect users against unintended needle sticks.

Increasingly such syringes are supplied prefilled to the end users for self injection, for instance for diabetics. The use of the syringe in untrained hands, particularly with older patients, leads often to damage to the needle before or after use. Furthermore even if the protective cap can be removed, the unskilled user often touches or otherwise comprises the sterility of the needle, and many people are so scared of hypodermic syringes that they cannot be brought to self inject.

OBJECTS OF THE INVENTION

It is therefore an object of the present invention to provide an improved protector for a syringe.

Another object is the provision of such an improved protector for a syringe which overcomes the above-given disadvantages, that is which protects and maintains the needle itself sterile, and that allows even persons shy of hypodermics to self inject.

SUMMARY OF THE INVENTION

A syringe has a syringe body having an outer end, a needle holder on the outer end, a needle fixed on the needle holder so that liquid in the body can be expressed through the needle, and a cap removably fitted to the body over the needle holder and enclosing the needle holder and needle. According to the invention a flexible envelope engaged over the needle has an inner end fixed to the needle holder and an outer end adapted to be easily pierced by the needle. The envelope is compressible parallel to the needle.

Thus with this system once the cap is removed, the needle remains inside the protective envelope where it is hidden from view and perfectly sterile. The user can self inject simply by pressing the end of the envelope against his or her skin and pushing the needle through the envelope into the skin, without in fact exposing the actual needle to daylight. Perfect sterility is maintained and persons squeamish about needles can use the system without problems.

According to the invention the envelope is generally cylindrical and formed as a cuff, for instance with annular corrugations allowing it to compress axially very easily. The end of the envelope can be made particularly thin for easy piercing by the needle, or can have a hole or thin region for such piercing.

The envelope in accordance with the invention is formed of thin elastically deformable material. It can be made of an elastomer such as natural or synthetic rubber. Furthermore it can be provided with a coil spring compressible parallel to the needle. Such a spring makes the envelope fairly strong but still easy to compress axially, that is parallel to the needle.

The needle holder according to the invention fits complementarily in the cap. More particularly the needle holder and cap are joined together at a weakened region which can be fractured to separate the holder and cap. Furthermore the needle holder is formed around the needle with a stop limiting injection depth. This stop can be an annular extension or shoulder formed on the body around the needle. Alternately the envelope when compressed limits injection depth of the needle.

When the protector with the needle are separate from the actual body of the syringe or carpule the cap has an open end provided with a removable seal to preserve sterility of the needle. In addition the holder can be provided with a luer connection for the syringe body. When the body is a carpule provided with an annular cap the needle holder has a retainer engaging the annular cap.

BRIEF DESCRIPTION OF THE DRAWING

The above and other objects, features, and advantages it will become more readily apparent from the following description, reference being made to the accompanying drawing in which:

FIGS. 1a through 1d are axial sections through a syringe showing use of the protector according to the invention;

SPECIFIC DESCRIPTION

Figure 2:
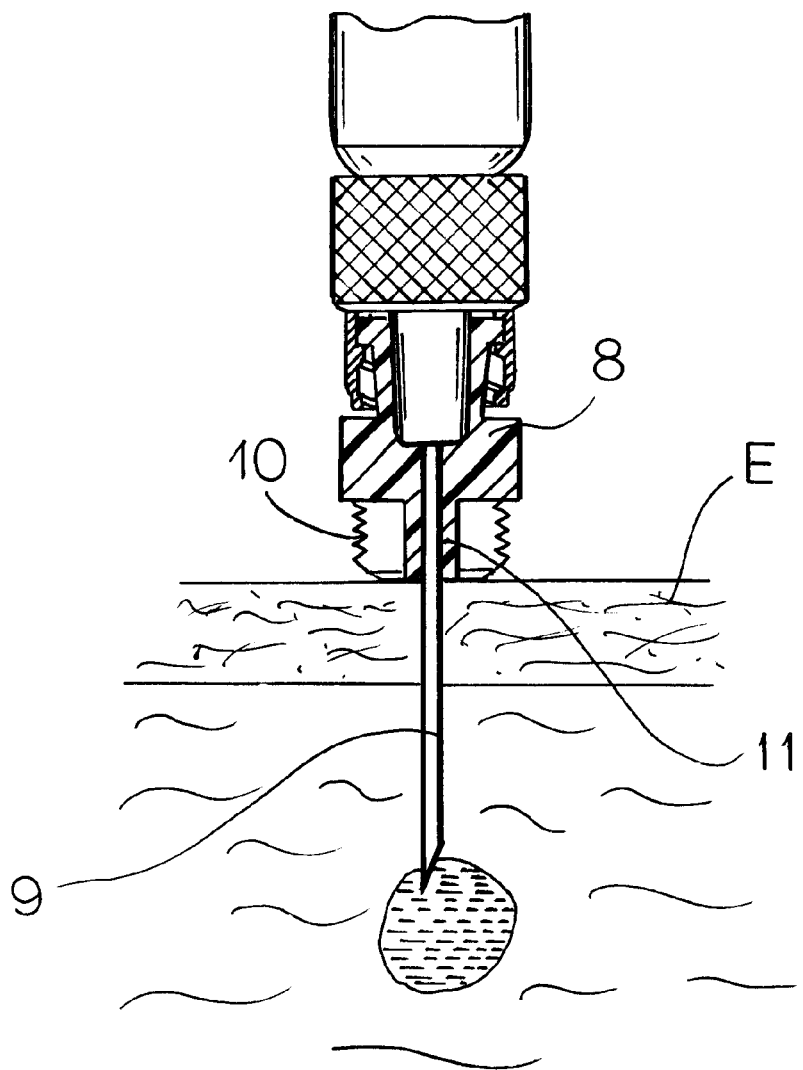
FIG. 2 is a section showing use of the protected syringe in accordance with the invention.
Figure 3A:
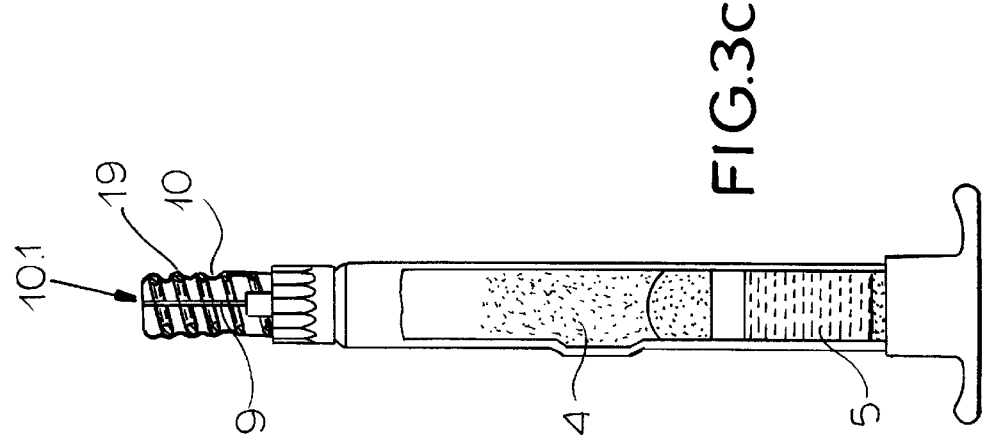
FIGS. 3a through 3c are axial sections through a carpule-type syringe with the protector of this invention.
Figure 3B:
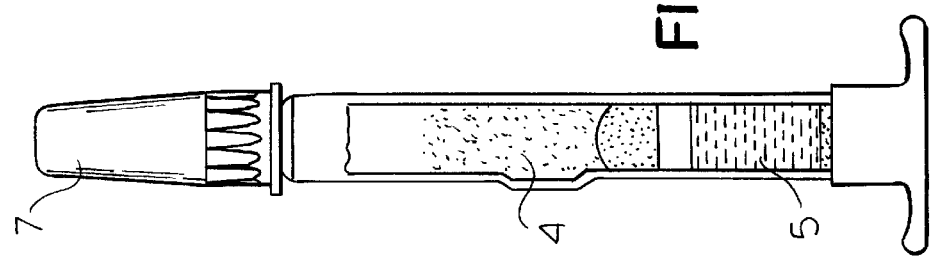
Figure 3C:
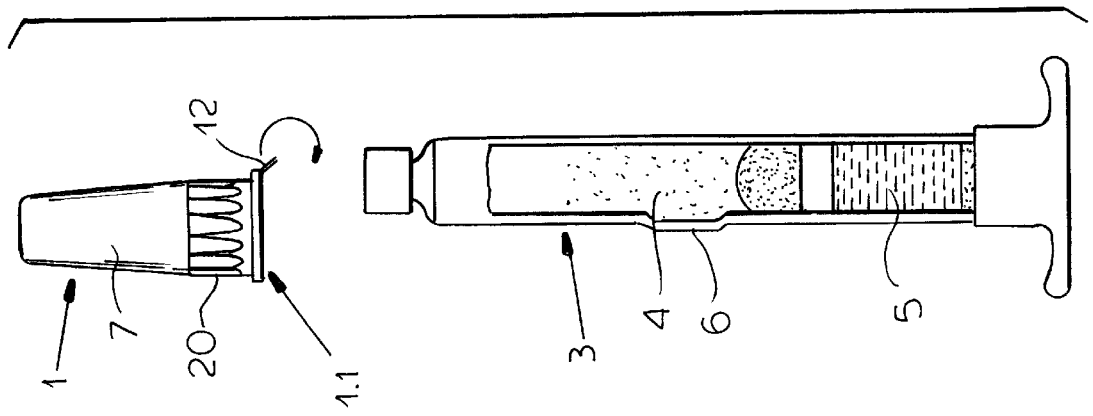
Figure 4:
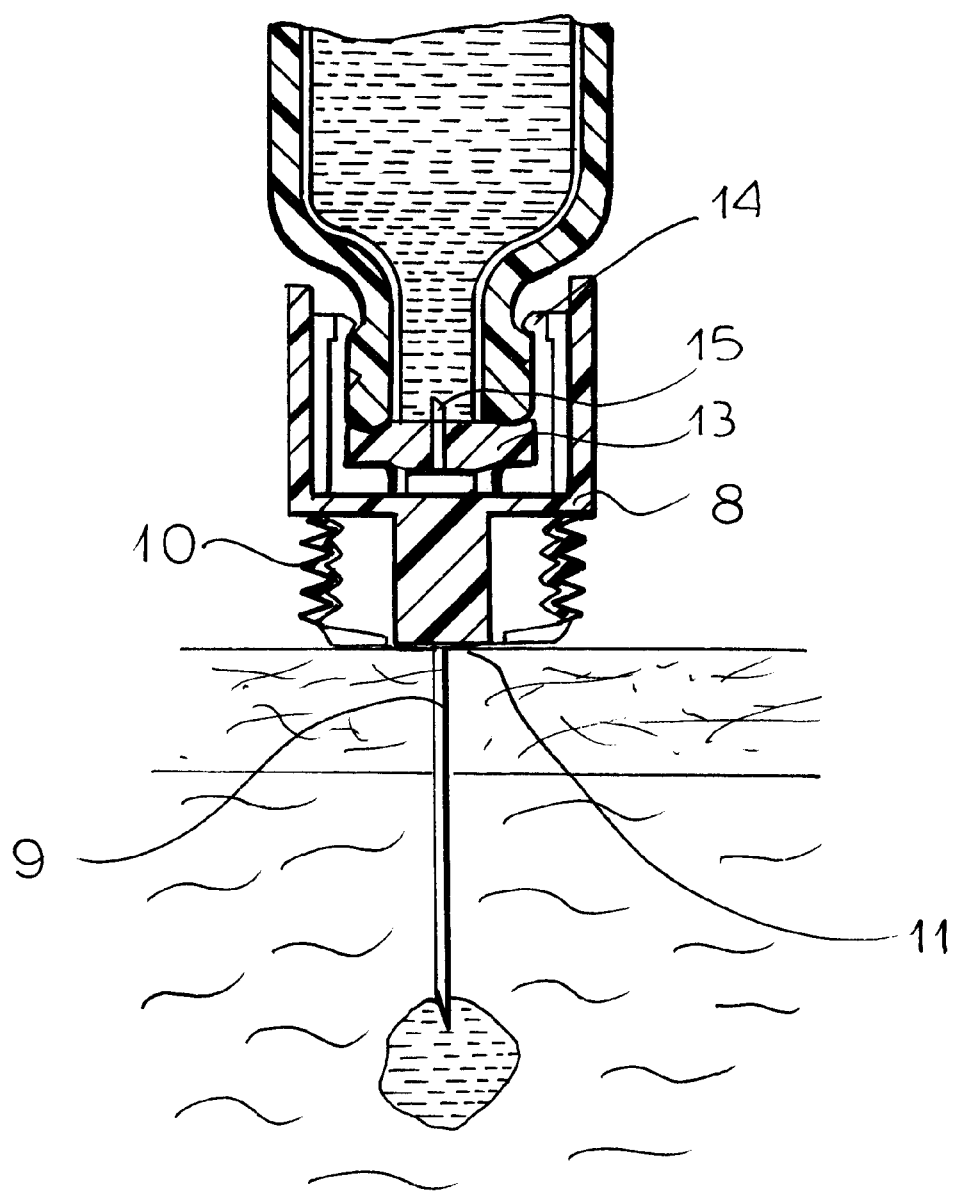
FIG. 4 is a view like FIG. 2 showing the syringe of FIGS. 3a–3c.

As seen in FIGS. 1a, 1b, 1c, 1d, and 2 a protector 1 according to the invention is used on a syringe body 2 having a removable end cap 16 and plug 17. The body 2 has a plunger/partition 18 subdividing its interior into a pair of compartments 4 and 5 respectively filled with a medicament and its solvent and connectable via a bypass 6 when the plunger 18 is advanced as is well known in the art. This unit can be delivered to the end user as shown for immediate one-time use.

The protector 1 according to the invention comprises a cup- or thimble-shaped cap 7 whose end 1.1 is normally closed by a removable tear sheet 12 and which has a base 8 carrying a standard cannula or needle 9 adapted to fit into the end of the body 2, once the breakaway cap 16 and plug 17 are removed. Inside the cap 7, which can be snapped off the base 8 as shown in FIGS. 1c and 1d, is a flexible protector enveloper or sheath 10 having one end sealed hermetically to the base 8 around the needle 9 and an opposite closed end 10.1 that is relatively thin and easily pierced by the outer end of the needle 9.

To use the assembly of FIGS. 1a–2, the tear sheet 12 is pulled off the protector 1 and the cap 16 and plug 17 are removed (FIG. 1b) from the body 2, then the protector 1 is fitted to the syringe end so that the base 8 and needle 9 are fitted in place as is standard (FIG. 1c). The cap 7 is then snapped off the holder 8 at a weakened region 20 (FIG. 1d) leaving the needle 9 wholly hermetically contained in the envelope 10 which is seen to have circumferential corrugations facilitating its compression parallel to an axis A of the assembly. The needle 9 can then be poked into the patient's epidermis E as shown in FIG. 2 simply by pushing the needle 9 through the end 10.1 and causing the sheath 10 to compress axially. A small-diameter extension 11 of the base 8 surrounding the needle 9 serves as a stop determining injection depth and allows the sheath 10 to be compressed behind it.

The system of FIGS. 3a, 3b, 3c, and 4 is essentially the same as that described above except that the syringe here is a carpule 3. The envelope 10 here is internally provided with a coil spring 19 that holds it in the extended position but allows it to be compressed axially, the compressed envelope itself acting as an injection-depth stop. In addition the system here has a cap 13 with a retainer 14 and the needle 9 has a pointed inner end 15. Otherwise this arrangement functions identically to that of FIGS. 1a–1d and 2.

We claim:

1. A syringe comprising:
   a carpule body having an outer end and provided with an annular cap;
   a needle holder on the outer end and having a retainer engaging the annular cap;
   a needle fixed on the needle holder, whereby liquid in the body can be expressed through the needle;
   a cap removably fitted to the body over the needle holder and enclosing the needle holder and the needle; and
   a flexible envelope engaged over the needle and having an inner end fixed to the needle holder and an outer end adapted to be easily pierced by the needle, the envelope being compressible parallel to the needle.

2. The syringe defined in claim 1 wherein the envelope is generally cylindrical and formed as a cuff.

3. The syringe defined in claim 1 wherein the envelope is formed of thin elastically deformable material.

4. The syringe defined in claim 1 wherein the envelope is made of an elastomer.

5. The syringe defined in claim 1 wherein the envelope is provided with a coil spring compressible parallel to the needle.

6. The syringe defined in claim 1 wherein the needle holder fits complementarily in the cap.

7. The syringe defined in claim 1 wherein the needle holder is formed around the needle with a stop limiting injection depth.

8. The syringe defined in claim 7 wherein the stop is an annular extension formed on the body around the needle.

9. The syringe defined in claim 1 wherein the envelope when compressed limits injection depth of the needle.

10. The syringe defined in claim 1 wherein the cap has an open end provided with a removable seal.

11. The syringe defined in claim 1 wherein the holder is provided with a Luer connection for the syringe body.

12. A syringe comprising:
    a carpule having an outer end;
    an annular cap on the carpule;
    a needle holder on the outer end and having a retainer engaging the annular cap;
    a needle fixed on the needle holder, whereby liquid in the carpule can be expressed through the needle;
    a cap removably fitted to the carpule over the needle holder and enclosing the needle holder and the needle, the needle holder and the cap being joined together at a weakened region which can be fractured to separate the holder and the cap; and
    a flexible envelope engaged over the needle and having an inner end fixed to the needle holder and an outer end adapted to be easily pierced by the needle, the envelope being compressible parallel to the needle.

* * * * *